(12) United States Patent
Li et al.

(10) Patent No.: US 11,682,547 B1
(45) Date of Patent: Jun. 20, 2023

(54) ULTRAVIOLET LAMP TUBE AND GAS DISCHARGE UV LAMP

(71) Applicant: Langsim Optoelectronic Technologies (Guangdong) Limited, FosGuangdong (CN)

(72) Inventors: Jiawei Li, Xiamen (CN); Zhen Li, Hangzhou (CN)

(73) Assignee: Langsim Optoelectronic Technologies (Guangdong) Limited, Foshan (CN)

( * ) Notice: Subject to any disclaimer, the term of this patent is extended or adjusted under 35 U.S.C. 154(b) by 0 days.

(21) Appl. No.: 17/811,537

(22) Filed: Jul. 8, 2022

(30) Foreign Application Priority Data

Feb. 10, 2022 (CN) .......................... 202220273306.4
Apr. 28, 2022 (CN) .......................... 202221017401.4

(51) Int. Cl.
*H01J 65/00* (2006.01)
*H01J 61/02* (2006.01)
*H01J 61/34* (2006.01)
*H01J 61/33* (2006.01)
*G02B 5/26* (2006.01)
*A61L 2/10* (2006.01)
*G02B 5/08* (2006.01)

(52) U.S. Cl.
CPC .............. *H01J 61/025* (2013.01); *A61L 2/10* (2013.01); *G02B 5/0808* (2013.01); *G02B 5/26* (2013.01); *H01J 61/33* (2013.01); *H01J 61/34* (2013.01); *A61L 2202/11* (2013.01)

(58) Field of Classification Search
CPC .......... H01J 61/33; H01J 61/34; H01J 61/025; H01J 65/00; H01J 65/04
USPC ......................................................... 313/607
See application file for complete search history.

(56) References Cited

U.S. PATENT DOCUMENTS

| 6,398,970 B1 * | 6/2002 | Justel ...................... H01J 65/04 313/643 |
| 7,687,997 B2 * | 3/2010 | Gaertner ............... H01J 65/046 313/634 |
| 8,164,239 B2 * | 4/2012 | Fujisawa ................. H01J 65/00 313/634 |
| 2001/0022499 A1 * | 9/2001 | Inayoshi ............... B08B 7/0057 313/607 |
| 2007/0236119 A1 * | 10/2007 | Espiau .................... H01J 61/35 313/110 |

FOREIGN PATENT DOCUMENTS

JP     2021072274 A   *   5/2021         H01J 61/025
KR     19990028639 A   *   4/1999

* cited by examiner

*Primary Examiner* — Christopher M Raabe
(74) *Attorney, Agent, or Firm* — Fox Rothschild LLP

(57) ABSTRACT

The present application discloses an ultraviolet lamp tube and a novel gas discharge UV lamp, which, through unique coating methods, can ensure monochromaticity of light output of the light source, while increasing the luminous angle of the ultraviolet lamp tube, thus effectively improving the light efficiency, simplifying structure, and greatly reducing production costs.

20 Claims, 2 Drawing Sheets

ULTRAVIOLET LAMP TUBE AND GAS DISCHARGE UV LAMP

CROSS-REFERENCE TO RELATED APPLICATIONS

This application claims priority under 35 U.S.C. § 119(a) to Chinese Patent Application No. 202220273306.4, filed on Feb. 10, 2022, and Chinese Patent Application No. 202221017401.4, filed on Apr. 28, 2022, with the China National Intellectual Property Administration, the disclosures of both of which are incorporated herein by reference in their entirety.

FIELD OF THE DISCLOSURE

The present invention relates to the technical field of ultraviolet lamps, in particular, to an ultraviolet lamp tube and a noval gas discharge UV lamp, with a high luminous efficiency.

BACKGROUND OF THE DISCLOSURE

Ultraviolet light sources are mostly used for medical purposes such as sterilization and disinfection, analysis purposes such as changes based on irradiated ultraviolet light, industrial purposes such as ultraviolet curing, cosmetic purposes such as ultraviolet tanning, and other purposes such as insect trapping, counterfeit currency identification, etc.

The existing UV lamp is filtered by a filter to filter out useless wavelength bands, but the structure still has the defects such as small light-emitting angle and low light efficiency, as well as complex structures and high costs.

A gas discharge lamp is a type of electric light source that converts electrical energy into light through electrical discharge of gases. Generally, a gas discharge lamp releases the electrical energy through the gas discharge mode to produce light waves, and the level of brightness depends on the amount of energy released during the discharge, which is provided by the energy driving power supply. Among them, the ultraviolet lamp is one type of the gas discharge lamps. However, the existing ultraviolet lamps have low luminous efficiency, and cannot selectively transmit a single wavelength band, and cannot meet needs of humans.

SUMMARY OF THE DISCLOSURE

To overcome the above-mentioned defects of the existing ultraviolet lamps, the present disclosure provides an ultraviolet lamp tube, which has the characteristics of large luminous angle, high luminous efficiency, simple structure and low cost, as well as a novel, highly efficient gas discharge UV lamp that can find wide applications.

In one aspect, the present disclosure provides an ultraviolet lamp tube, comprising an inner tube and an outer tube, the inner tube penetrating through inside of the outer tube, an excitation chamber formed between the inner tube and the outer tube; an inner electrode arranged in the inner tube; the outer tube comprising a curved surface portion and a flat surface portion, the curved surface portion and the flat surface portion connected to each other, wherein the curved surface portion is an arc-shaped surface arranged coaxially with the inner tube, and the flat surface portion is a plane; and wherein a first film layer is arranged on the flat surface, a second film layer is arranged on the curved surface, and the outer surface of the curved portion is provided with an outer electrode.

In one embodiment, the arc-shaped surface has a central angle in the range of from 240° to 260°. In one embodiment, sometimes preferably, the central angle of the arc-shaped surface is from 245° to 255°. In one embodiment, sometimes more preferably, the central angle of the arc-shaped surface is 250°±2°.

In one embodiment, the wavelengths of the wave bands that the first film layer and the second film layer can transmit are different.

In one embodiment, the first film layer is a filter film layer, and the filter film layer has a property of transmitting selected wavelengths.

In one embodiment, the filter film layer is a single-wavelength film layer, and the single-wavelength coating has a property of light unity; the single-wavelength coating can only transmit a single-wavelength wave band to the outside of the flat surface portion.

In one embodiment, the first film layer is plated on the outer surface of the flat surface portion.

In one embodiment, the second film layer is a reflective film layer, and the reflective film layer has a light reflection property and is used to reflect any wavelength band back to the excitation chamber.

In one embodiment, the reflective film layer is a reflective coating spray coated on the outer surface of the curved portion.

In one embodiment, the second film layer is a clutter wave film layer, and the clutter wave film layer can transmit the wavelength bands that cannot pass through the first film layer, and at the same time reflect the wavelength band that can pass through the first film layer back to the excitation chamber.

In one embodiment, the clutter wave film layer is coated on the outer surface of the curved portion.

In one embodiment, the second film layer is a metal reflective plating layer, and the metal reflective plating layer reflects the clutter waves that cannot pass through the first film layer to the inner tube, and to be absorbed by the inner electrode; at the same time, the metal reflective plating layer reflects the wavelength band that can pass through the first film layer back to the excitation chamber.

In one embodiment, the metal reflective plating layer is coated on the outer surface of the curved portion.

In one embodiment, the metal reflective plating layer also serves as an outer electrode, and the metal reflective plating is a silver reflective coating or aluminum reflective coating, which has a large reflection coefficient for light waves.

In another aspect, the present disclosure provides a gas discharge UV lamp, comprising an inner tube and an outer tube arranged coaxially; an inner electrode installed in the inner tube; and a sealed ionization discharge chamber formed between the inner tube and the outer tube; wherein the outer wall of the outer tube is coated with coating A; the outer wall of the outer tube is also plated with a metal reflective plating, the reflective layer also serves as an outer electrode; the coating A and the metal reflective plating are arranged opposite to each other; and the metal reflective plating is a silver reflective coating or aluminum reflective coating.

In one embodiment, the ionization discharge chamber contains a gas, in particular a noble gas such as neon, argon, krypton, or xenon, or a combination thereof. When the inner electrode and the outer electrode are charged with electricity, through the arc discharge of the inner electrode and the outer electrode, the noble gas in the chamber is excited to produce atomic transitions; when the atoms of the noble gas return from an excited state to the ground state, the internal energy of the atoms is released in the form of radiation of lights. Through selection of the gas, a desired wavelength, thus color, of the light emitted can be obtained.

In one embodiment, sometimes preferred, the coating A is a film coating that can transmit a single wavelength band; and the coating A can only transmit a wavelength band of a single wavelength out of the outer tube.

In one embodiment, sometimes preferred, the metal reflective plating reflects the clutter waves that cannot pass through the coating A to the inner tube, transmits them to the inner electrode through the inner tube, and to be absorbed by the inner electrode; at the same time, the metal reflective plating reflects the light to the side of coating A, which transmits the light waves of a useful wavelength out of the outer tube.

In one embodiment of this aspect, the gas discharge UV lamp comprises a UV lamp tube in any one of the embodiments disclosed herein, wherein the outer tube comprises a curved surface portion and a flat surface portion, the curved surface portion and the flat surface portion connected to each other, and wherein the curved surface portion is an arc-shaped surface arranged coaxially with the inner tube, and the flat surface portion is a plane.

In one embodiment, the arc-shaped surface has a central angle in the range from 240° to 260°. In one embodiment, sometimes preferably, the central angle of the arc-shaped surface is from 245° to 255°. In one embodiment, sometimes more preferably, the central angle of the arc-shaped surface is 250°±2°.

In another aspect, the present disclosure provides a device comprising a novel ultraviolet lamp tube or gas discharge UV lamp according to any embodiment disclosed herein, for example, while not intended to be limiting, the novel ultraviolet lamp tube or gas discharge UV lamp can be used in a disinfection device for antibacterial and/or antiviral applications, preferably in a space occupied by humans and/or animals, including but not limited to domestic pets or farm-raised animals, such as cats, dogs, monkeys, horses, pigs, cattles, poultry, or the like.

Compared with the existing technology, the present disclosure provides various advantages.

For example, the ultraviolet lamp tube of the present disclosure filters lights by means of film coating, which can ensure the monochromaticity of the wavelength of light emitted by the light source, and the volume of the ultraviolet lamp tube can be reduced by means of film coating, which is convenient for use; by means of arranging the outer tube with a combination of the curved portion and the flat portion, and plating the second film layer and the first film layer with different wavelength transmitting properties on the curved portion and the flat portion, respectively, the light emission from the plane is achieved and the light output efficiency of the UV lamp is effectively improved; designing the ultraviolet lamp tube in a non-complete circular cylindrical shape can effectively increase the light-emitting angle of the UV lamp; by distinguishing the flat portion and the curved portion to locate the position of the light-emitting surface, it is easy to use, and during the coating process, the flat coating position is determined by locating the flat portion position, which greatly improves the production efficiency, and also effectively improves the coating quality and reduces costs.

Similarly, the gas discharge UV lamp of the present disclosure, through arranging a plated coating A and a metal reflective plating on the outer wall of the outer tube, wherein the coating A can transmit a useful single wavelength band outside of the outer tube, whereas the metal reflective plating adopts a silver reflective plating or aluminum reflective coating, which reflects the light to the coating A surface, among other characteristics, can ensure the single wavelength of light output of the light source, and at the same time the coating A and metal reflective plating can improve the luminous efficiency of the gas discharge UV lamp.

Other aspects or advantages of the disclosure will be better appreciated in view of the following drawings, detailed description, examples, and claims.

BRIEF DESCRIPTION OF THE DRAWINGS

In FIGS. 1 to 3: 100, inner tube; 200, outer tube; 210, curved surface portion; 211, second film layer; 220, flat surface portion; 221, first film layer; 300, excitation chamber; 400, inner electrode; 500, outer electrode.

DETAILED DESCRIPTION OF THE DISCLOSURE

Figure 1:
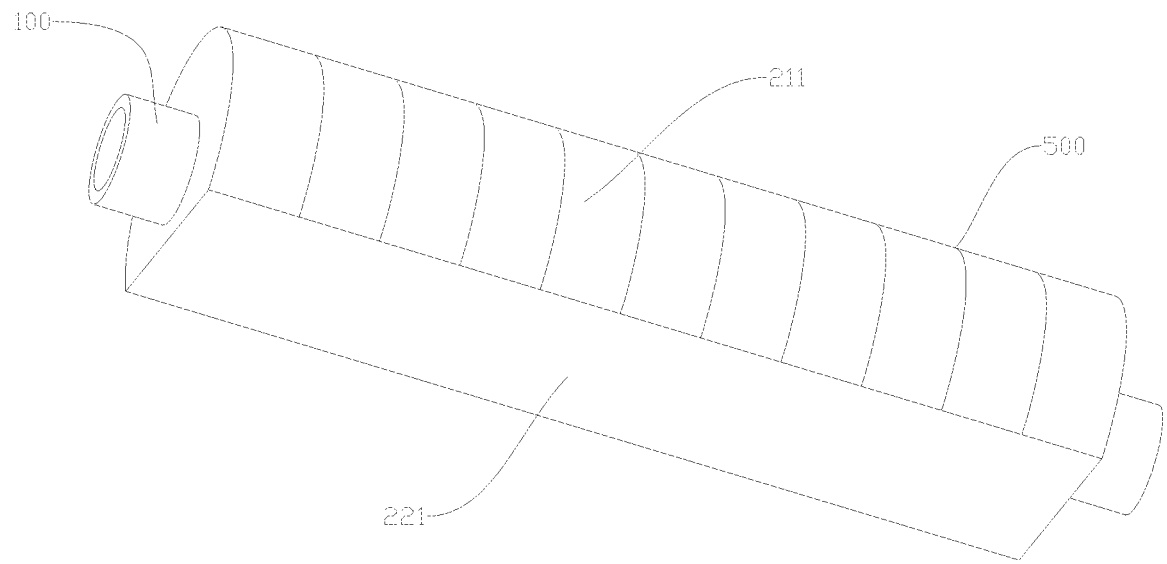
FIG. 1 is a three-dimensional view of an illustrative ultraviolet lamp tube.

The present invention will be further described with reference to the accompanying drawings and specific embodiments. It should be noted that, so long as no conflicts are resulted, the embodiments or technical features described below can be reasonably combined to form new embodiments. Unless otherwise specified, the materials and equipment used in the embodiments can be purchased from the market. Examples of such embodiments are illustrated in the accompanying drawings, wherein the same or similar reference numerals refer to the same or similar elements or elements having the same or similar functions throughout. The embodiments described below with reference to the accompanying drawings are illustrative and only used to explain the present application and should not be construed as limiting the present application. The drawings are all simplified schematic diagrams, and only illustrate the basic structure of the present disclosure in a schematic manner, so they only illustrate the structures related to the present disclosure and should not be interpreted as limiting the invention.

In the description of this application, it is to be understood that the terms "inner", "outer", "inside", "outside", "between", etc., refer to the orientation or positional relationship based on the orientation or positional relationship shown in the accompanying drawings, which is only for the convenience of describing the present application and simplifying the description, rather than indicating or implying that the device or element referred to must have a specific orientation, or constructed or operated in a particular orientation, and is therefore not to be construed as a limitation of the present application. In the description of this application, "plurality" means two or more, unless it is precisely and specifically defined otherwise.

In the description of the present application, it should be noted that, unless otherwise expressly specified and defined, the terms "install", "arrange", "connect", "connected", or the like, should be understood in a broad sense, for example, it can be a fixed connection, a detachable connection, or an integral connection; it can be a mechanical connection, or an electrical connection; it can be directly connected or can be an indirect connection via an intermediary media, can be the internal connection of two elements or the interaction relationship between the two elements of a unit. For those of ordinary skill in the art, the specific meanings of the above terms in this application can be understood according to specific situations.

The terms "first", "second", and the like, in the description and claims of the present application and the above drawings are used to distinguish similar objects and are not necessarily used to describe a specific order or sequence. Furthermore, the terms "comprising" and "having", and any variations thereof, are intended to cover non-exclusive inclusion, for example, a process, method, system, product or device comprising a series of steps or units is not necessarily limited to those expressly listed, rather, may include other steps or units not expressly listed or inherent to these processes, methods, products or devices.

The following non-limiting examples further illustrate certain aspects of the present disclosure.

EXAMPLES

Example 1

Figure 2:
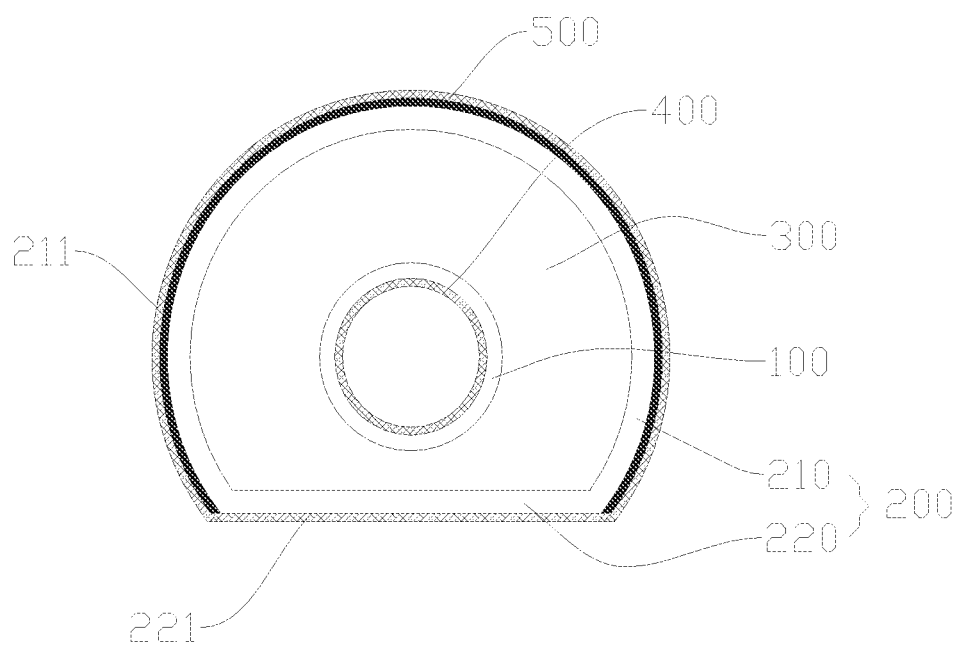
FIG. 2 is a schematic cross-sectional view of the illustrative ultraviolet lamp tube.
Figure 3:
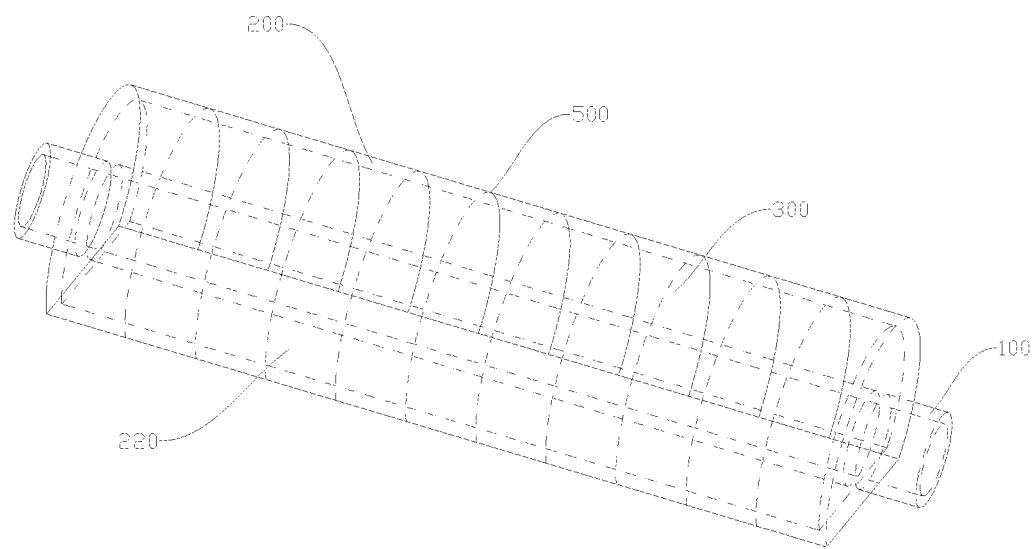
FIG. 3 is a perspective view of the internal structure of the illustrative ultraviolet lamp tube.

Referring to FIG. 1-3, a UV lamp tube includes an inner tube 100 and an outer tube 200, the inner tube 100 penetrates through inside the outer tube 200; an excitation chamber 300 is formed between the inner tube 100 and the outer tube 200; an inner electrode 400 is arranged in the inner tube 100. Specifically, the inner electrode 400 is arranged on the inner wall of the inner tube 100; an outer electrode 500 is arranged on the outer surface of the curved surface portion 210 of the outer tube 200.

Referring to the cross-sectional view of the UV lamp tube shown in FIG. 2, the outer tube 200 includes a curved surface portion 210 and a flat surface portion 220 connected to each other, the curved surface portion 210 is a circular arc-shaped surface coaxially arranged with the inner tube 100, and the flat surface portion 220 is a plane;

The curved portion 210 is plated with a second film layer 211, and the flat surface portion 220 is plated with a first film layer 221; the wavelengths that the first film layer 221 and the second film layer 211 can transmit are different.

The ultraviolet lamp tube in this embodiment filters lights by means of film coating, which can ensure the unity of the wavelength of light emitted by the light source, and the volume of the ultraviolet lamp can also be reduced by means of coating, which is convenient for use; by designing the outer tube 200 as a combination of curved surface portion 210 and flat surface portion 220, and coating the curved surface portion 210 and the flat surface portion 220 respectively with a second film layer 211 and a first film layer 221, which can transmit different wavelengths, so as to achieve light emission from the plane and effectively improve the luminous efficiency of the UV lamp tube; the luminous angle of the UV lamp tube can be effectively increased by designing the UV lamp tube in a non-completely circular cylindrical shape; the position of the light emitting surface can be set by distinguishing the flat surface portion 220 and the curved surface portion 210, which is convenient for use, and during the coating process, by locating the position of the flat surface portion 220 to determine the plane coating position, the production efficiency can be greatly improved, the coating quality can be effectively improved, and the cost can be reduced.

Example 2

A UV lamp tube as shown in FIG. 1-3, in this example, on the basis of Example 1, the first film layer 221 is a filter film layer, and the filter film layer has a property of transmitting selected wavelengths; the second film layer 211 is a reflective film layer, and the reflective film layer has light reflection properties.

The first film 221 can selectively transmit a single wavelength band required, such as 207 nm, 222 nm, 250 nm, 308 nm, etc.; The second film layer 211 is a reflective film layer that can reflect any wavelength band back to the excitation chamber 300.

By setting the second film layer 211 as a reflective film layer, the wavelength band projected to the second film layer 211 is reflected back to the excitation chamber 300, and then projected to the first film layer 221 through the reflection of the curved surface portion 210, and the filter film layer with a wavelength selection property transmits the desired wavelength band and filters out useless clutter waves, and also enhances the light efficiency of the UV lamp.

The second film layer 211 can be a metal reflective plating layer, also serves as an outer electrode, and the metal reflective plating is a silver reflective coating or aluminum reflective coating, which has a large reflection coefficient for light waves.

Example 3

A UV lamp tube as shown in FIG. 1-3, this example is based on Example 1. The first film layer 221 is a light filter coating, and the light filter coating has the property of transmitting selected wavelengths; the second film layer 211 is a clutter wave film layer, the clutter wave film layer can transmit the wavelength bands that cannot pass through the first film layer 221, and at the same time reflect the wavelength band that can pass through the first film layer 221 back to the excitation chamber 300, which is further projected to the first film layer 221 through reflection and emitted out.

The first film layer 221 can transmit useful single wavelength band, such as 207 nm, 222 nm, 250 nm, 308 nm, etc., while the second film layer 211 can project the wavelength bands that cannot pass through the first film layer 221, and at the same time reflect the single wavelength band that can pass through the first film layer 221 back to the excitation chamber 300.

The useful single wavelength band is reflected back to the excitation chamber 300 through the clutter wave film layer, and projected to the first film layer 221 through reflection and emitted out, which effectively improves the light efficiency of the ultraviolet lamp; the wavelength bands that cannot pass through the film layer 221 are emitted out by the second film layer 211.

In some other embodiments, the first film layer 221 is coated on the outer surface of the flat surface portion 220, which is beneficial to increase the volume of the excitation chamber 300 and improve the light efficiency. The second film layer 211 is a reflective coating spray coated on the outer surface of the curved surface portion 210, or a clutter wave coating coated on the outer surface of the curved surface portion 210, which is also beneficial to increase the volume of the excitation chamber 300 and improve the light efficiency. Further, by means of coating, while improving the light efficiency, it also makes the structure more simple and compact and improves the practicability of the ultraviolet lamp tube.

This disclosure adopts the method of film coating for filtering light, which can ensure the monochromaticity of the light output of the light source. Secondly, the method of film coating can enhance the output power of ultraviolet light, improve the photoelectric conversion efficiency, and at the same time, the luminous angle of the ultraviolet lamp can be effectively increased by the area ratio of the first film layer 221 and the second film layer 211, thus effectively improving the light efficiency of the ultraviolet lamp tube.

Example 4

Figure 4:
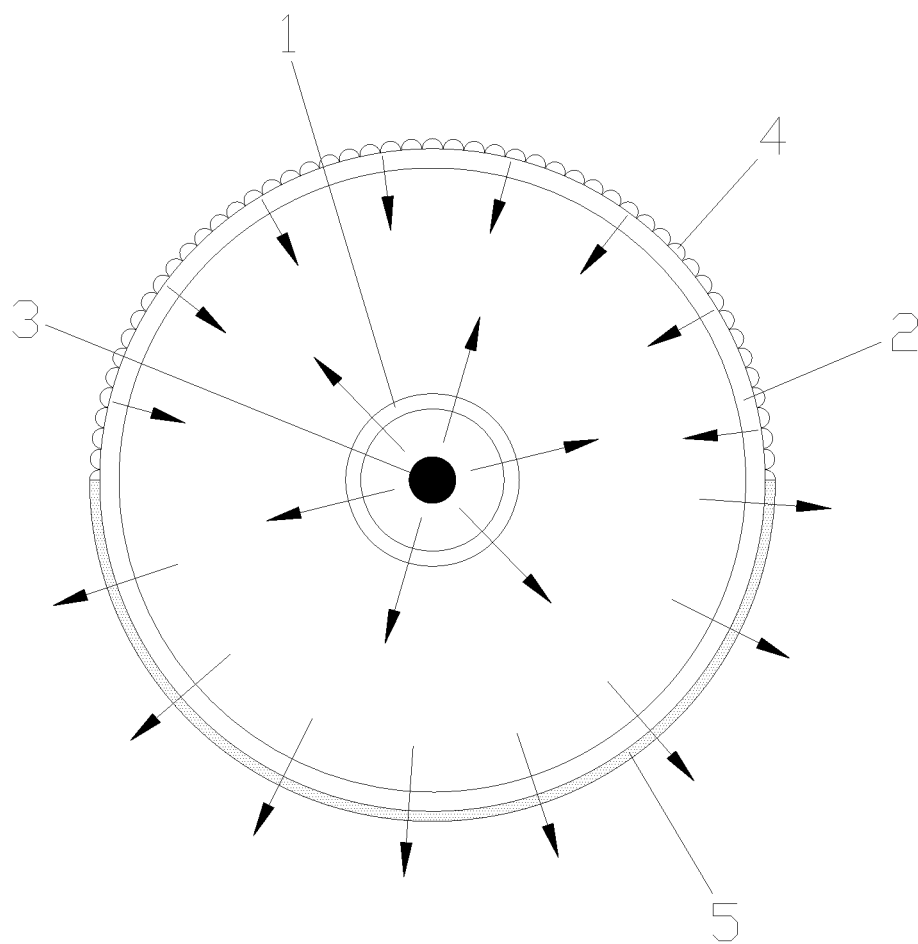
FIG. 4 is a schematic structural diagram of an illustrative gas discharge lamp, where: 1—inner tube; 2—outer tube; 3—inner electrode; 4—metal reflective plating; 5—coating A.

FIG. 4 illustrates a noval gas discharge UV lamp, comprising an inner tube 1 and an outer tube 2 arranged coaxially; inside the inner tube 1 is installed an inner electrode 3; a sealed ionization discharge chamber is formed between the inner tube 1 and the outer tube 2; the outer wall of the outer tube 2 is plated with coating A 5; the outer wall of the outer tube 2 is plated with a metal reflective coating 4, the reflective layer also acts as an outer electrode; the coating A 5 and the metal reflective coating 4 are arranged opposite to each other; and the metal reflective coating 4 is silver reflective coating or aluminum reflective coating. The coating A 5 is a coating that can transmit a single wavelength band; the coating A 5 can only transmit a wavelength band of a single wavelength out of the outer tube 2; the metal reflective plating 4 reflects the clutter waves that cannot pass through the coating A 5 to the inner tube 1, which are transmitted to the inner electrode 3 through the inner tube 1, and absorbed by the inner electrode 3; at the same time, the metal reflective plating 4 reflects the light to the side of coating A 5 which transmits the light band with useful light wavelengths out of the outer tube 2.

The gas discharge UV lamp can ensure the single wavelength of light output of the light source, through arranging a plated coating A 5 and a metal reflective plating 4 on the outer wall of the outer tube, wherein the coating A 5 is a coating that can transmit a single wavelength band and transmit the useful single wavelength band to the outside of the outer tube 2, whereas the meal reflective plating 4 adopts a silver reflective coating or aluminum reflective coating, which has a large reflection coefficient for light waves. When the light beam radiates on the metal surface from inside of the chamber, the metal reflective surface reflects the light to the coating A surface, and the metal coating is used as the reflective medium, coupled with the single wavelength characteristic of coating A.

In the description of this specification, the reference terms such as "one embodiment," "some embodiments," "exemplary embodiment," "example," "specific example," or "some examples", etc., mean a particular feature, structure, material, or characteristic described in this embodiment or an example is included in at least one embodiment or illustrative example of the present disclosure. In this specification, schematic representations of the above terms do not necessarily refer to the same embodiment or example. Furthermore, the particular features, structures, materials or characteristics described may be combined in a suitable manner in any one or more embodiments or examples.

While only certain components and embodiments of the present application have been illustrated and described, many modifications and changes can occur to those skilled in the art without departing from the scope and spirit of the claims (e.g., variations in size, dimensions, configuration, shape and proportions, mounting arrangements, material usage, color, orientation, etc. of individual elements). It will be apparent to those skilled in the art that the present disclosure is not limited to the details of the above-described exemplary embodiments, and the present disclosure can be implemented in other specific forms. Therefore, the embodiments are to be regarded in all respects as illustrative and non-limiting, and it is therefore intended to embrace within the present disclosure all changes that come within the meaning and range of equivalents of the claims. Any reference symbols or numbers to the drawings in the claims shall not be construed as limiting the relevant claims.

What is claimed is:

1. An ultraviolet lamp tube, comprising an inner tube and an outer tube, the inner tube installed to penetrate through inside of the outer tube, wherein an excitation chamber is formed between the inner tube and the outer tube; an inner electrode arranged in the inner tube; wherein the outer tube comprises a curved surface portion and a flat surface portion, the curved surface portion and the flat surface portion connected to each other, wherein the curved surface portion is an arc-shaped surface arranged coaxially with the inner tube, and the flat surface portion is a plane; and wherein a first film layer is arranged on the flat surface portion, and a second film layer is arranged on the curved surface portion, and an outer electrode is installed on outer surface of the curved surface portion.

2. The ultraviolet lamp tube of claim 1, wherein the first film layer and the second film layer can transmit different wavelengths of wave bands.

3. The ultraviolet lamp tube of claim 2, wherein the first film layer is a light filtering film layer capable of transmitting selected wavelengths.

4. The ultraviolet lamp tube of claim 3, wherein the light filtering film layer is a single-wavelength coating, which can only transmit a single-wavelength waveband to outside of the flat surface portion.

5. The ultraviolet lamp tube of claim 1, wherein the first film layer is coated on outer surface of the flat surface portion.

6. The ultraviolet lamp of claim 3, wherein the second film layer is a reflective film layer capable of reflecting any wavelength band back to the excitation chamber.

7. The ultraviolet lamp tube of claim 6, wherein the reflective film layer is a reflective coating spray coated on the outer surface of the curved surface portion.

8. The ultraviolet lamp tube of claim 6, wherein the reflective film layer is a metal reflective plating layer coated on the outer surface of the curved surface portion.

9. The ultraviolet lamp tube of claim 8, wherein the metal reflective plating layer also serves as an outer electrode.

10. The ultraviolet lamp tube of claim 9, wherein the metal reflective plating layer is a silver reflective coating or aluminum reflective coating.

11. The ultraviolet lamp of claim 3, wherein the second film layer is a clutter wave film layer capable of transmitting wavelength band(s) that cannot pass through the first film layer, and at the same time, reflecting the wavelength band that can pass through the first film layer back to the excitation chamber.

12. The ultraviolet lamp of claim 11, wherein the clutter wave film layer is coated on the outer surface of the curved surface portion.

13. A gas discharge UV lamp, comprising an inner tube and an outer tube arranged coaxially; an inner electrode installed in the inner tube; wherein a sealed ionization discharge chamber is formed between the inner tube and the outer tube; wherein outer wall of the outer tube is plated with coating A, and the outer wall of the outer tube is also plated with a metal reflective coating, the reflective coating also serves as an outer electrode; and wherein the coating A and the metal reflective coating are arranged opposite to each other.

14. The gas discharge UV lamp of claim 13, wherein the coating A is a coating that can transmit a single wavelength band; and wherein the coating A can only transmit a single wavelength band to the outside of the outer tube.

15. The gas discharge UV lamp of claim 14, wherein the metal reflective coating reflects clutter waves that cannot pass through the coating A to the inner tube, and transmits them to the inner electrode through the inner tube, where they are absorbed by the inner electrode; at the same time, the metal reflective coating reflects the light to the coating A side which transmits the light waves of a useful wavelength out of the outer tube.

16. The gas discharge UV lamp of claim 15, wherein the metal reflective coating is a silver reflective coating or aluminum reflective coating.

17. A device comprising an ultraviolet lamp tube of claim 1.

18. The device of claim 17, which is a disinfection device.

19. A device comprising a gas discharge UV lamp of claim 13.

20. The device of claim 19, which is a disinfection device.

* * * * *